United States Patent [19]
Zavracky et al.

[11] Patent Number: 5,376,979
[45] Date of Patent: Dec. 27, 1994

[54] SLIDE PROJECTOR MOUNTABLE LIGHT VALVE DISPLAY

[75] Inventors: Matthew Zavracky, Attleboro; Stephen Offsey, Brookline; David Chastain, Acton; Michel Arney, Needham; Benjamin Beck, Boston; Gregory Hunter, Westwood; Kevin O'Connor, South Easton; Alan Richard, Wrentham, all of Mass.

[73] Assignee: Kopin Corporation, Taunton, Mass.

[21] Appl. No.: 106,071

[22] Filed: Aug. 13, 1993

Related U.S. Application Data

[63] Continuation-in-part of Ser. No. 16,138, Feb. 10, 1993, which is a continuation-in-part of Ser. No. 944,207, Sep. 11, 1992, which is a continuation-in-part of Ser. No. 823,858, Jan. 22, 1992, abandoned, and a continuation-in-part of Ser. No. 872,297, Apr. 22, 1992, Pat. No. 5,317,436, which is a continuation-in-part of Ser. No. 839,241, Feb. 20, 1992, which is a continuation-in-part of Ser. No. 636,602, Dec. 31, 1990, Pat. No. 5,206,749.

[51] Int. Cl.$^5$ ............................................. G03B 23/00
[52] U.S. Cl. ..................................... 353/122; 353/103
[58] Field of Search ......... 353/122, 103, 108, DIG. 3, 353/DIG. 5, 119, 120

[56] References Cited

U.S. PATENT DOCUMENTS

| | | | |
|---|---|---|---|
| 4,105,313 | 8/1978 | Attman | 353/122 |
| 4,393,380 | 7/1983 | Hosokawa et al. | 340/805 |
| 4,429,305 | 1/1984 | Hosokawa et al. | 340/784 |
| 4,582,395 | 4/1986 | Morozumi | 350/334 |
| 4,600,274 | 7/1986 | Morozumi | 350/339 |
| 4,653,862 | 3/1987 | Morozumi | 350/339 |
| 4,655,551 | 4/1987 | Washizuka et al. | 350/334 |
| 4,716,403 | 12/1987 | Morozumi | 340/702 |
| 4,740,782 | 4/1988 | Aoki et al. | 340/719 |
| 4,807,974 | 2/1989 | Hirai | 350/332 |
| 4,808,983 | 2/1989 | Benjamin et al. | 340/719 |
| 4,838,654 | 6/1989 | Hamaguchi et al. | 350/333 |
| 4,859,997 | 8/1989 | Bouron et al. | 340/752 |
| 4,886,343 | 12/1989 | Johnson | 350/335 |
| 4,917,468 | 4/1990 | Matsuhashi et al. | 350/332 |
| 4,952,031 | 8/1990 | Tsunoda et al. | 350/342 |
| 4,976,429 | 12/1990 | Nagel | 353/122 |
| 5,032,007 | 7/1991 | Silverstein et al. | 350/335 |
| 5,032,831 | 7/1991 | Kuijk | 340/784 |
| 5,095,304 | 3/1992 | Young | 340/766 |
| 5,115,232 | 5/1992 | Iizuka | 340/784 |
| 5,117,298 | 5/1992 | Hirai | 359/55 |
| 5,187,510 | 2/1993 | Vogeley et al. | 353/122 |

FOREIGN PATENT DOCUMENTS

| 0151508 | 8/1985 | European Pat. Off. |
| 63-055529 | 10/1988 | Japan |
| 1038727 | 9/1989 | Japan |

*Primary Examiner*—William A. Cuchlinski, Jr.
*Assistant Examiner*—William C. Dowling
*Attorney, Agent, or Firm*—Hamilton, Brook, Smith & Reynolds

[57] ABSTRACT

A housing is mountable on a carousel slide projector. The housing contains a movable light valve slide assembly that is coupled to a video signal source. The light valve slide assembly is movable between a position within the housing and a position outside the housing. When mounted on the slide projector, the light valve slide assembly can be moved into the projection chamber of the slide projector. The video signal source transmits a video signal to the light valve slide assembly, where the video signal is converted to a drive signal to actuate pixels on the light valve. The light valve thus generates a video image that is projected onto a viewing surface. Preferably the light valve is an active matrix liquid crystal display.

20 Claims, 13 Drawing Sheets

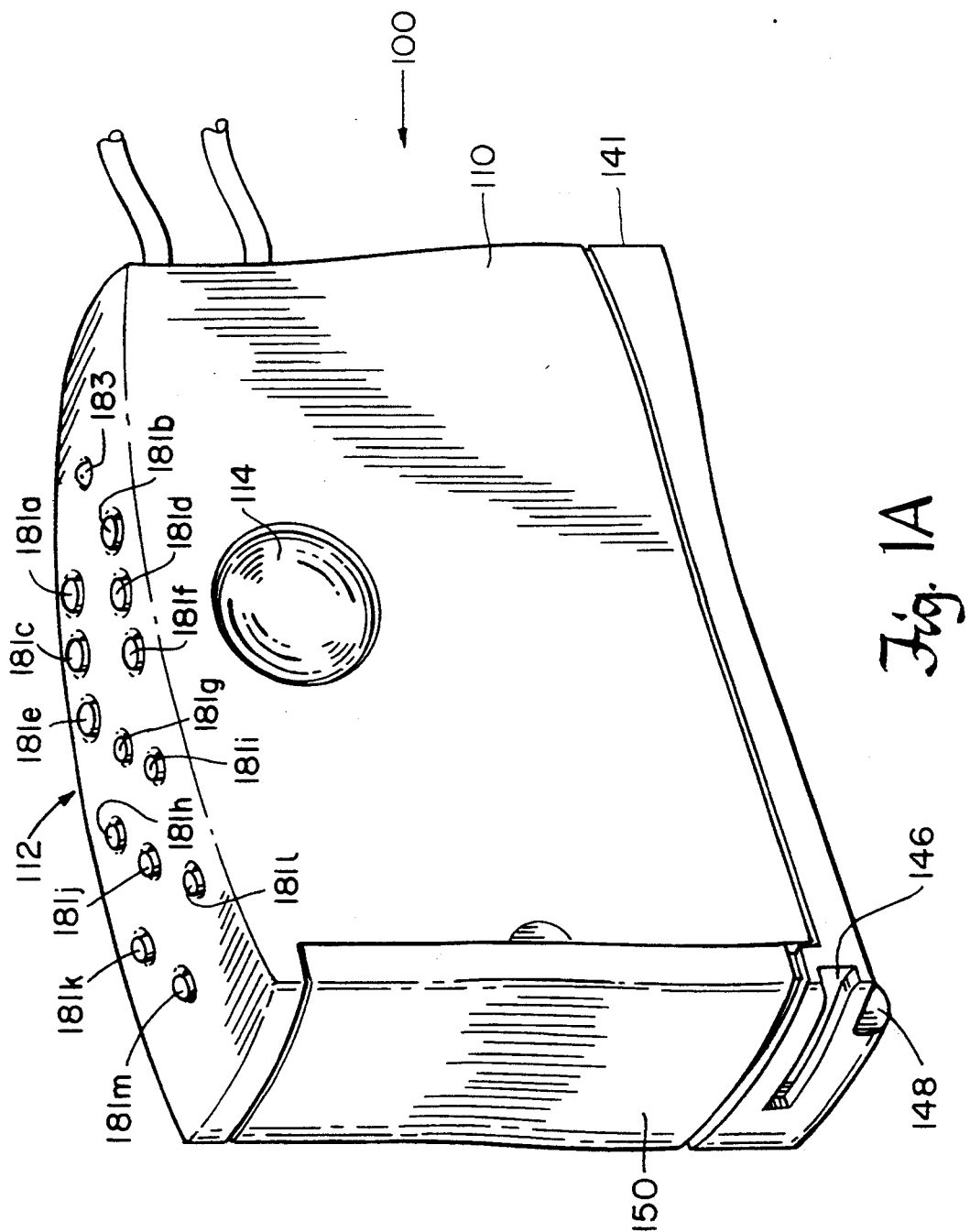

SLIDE PROJECTOR MOUNTABLE LIGHT VALVE DISPLAY

RELATED APPLICATION

This application is a continuation-in-part of U.S. patent application, Ser. No. 08/016,138 filed Feb. 10, 1993, which is a continuation-in-part of U.S. patent application, Ser. No. 07/944,207 filed on Sep. 11, 1992, which is a continuation-in-part of U.S. patent application, Ser. No. 07/823,858 filed on Jan. 22, 1992 and now abandoned, and Ser. No. 07/872,297, filed Apr. 22, 1992, (U.S. Pat. No. 5,317,436) which is a continuation-in-part of U.S. patent application, Ser. No. 07/839,241 filed Feb. 20, 1992, which is a continuation-in-part of U.S. patent application, Ser. No. 07/636,602 filed Dec. 31, 1990 (U.S. Pat. No. 5,206,749).

BACKGROUND OF THE INVENTION

Flat-panel displays are being developed which utilize liquid crystals or electroluminescent materials to produce high quality images. These displays are expected to supplant cathode ray tube (CRT) technology and provide a more highly defined television picture or computer monitor image. The most promising route to large scale high quality liquid crystal displays (LCDs), for example, is the active-matrix approach in which thin-film transistors (TFTs) are co-located with LCD pixels. The primary advantage of the active matrix approach using TFTs is the elimination of cross-talk between pixels, and the excellent grey scale that can be attained with TFT-compatible LCDs.

Flat panel displays employing LCDs generally include five different layers: a white light source, a first polarizing filter that is mounted on one side of a circuit panel on which the TFTs are arrayed to form pixels, a filter plate containing at least three primary colors arranged into pixels, and finally a second polarizing filter. A volume between the circuit panel and the filter plate is filled with a liquid crystal material. This material will rotate the polarization of light when an electric field is applied across the material between the circuit panel and a ground affixed to the filter plate. Thus, when a particular pixel of the display is turned on, the liquid crystal material rotates polarized light being transmitted through the material so that the light will pass through the second polarizing filter.

SUMMARY OF THE INVENTION

A preferred embodiment of the present invention relates to projection display devices (i.e. monitors and image projectors) including methods of fabricating such devices using thin films of single crystal silicon in which a light valve matrix (or matrices) is formed for controlling images produced by these devices. In accordance with the present invention, projection display devices employing high density single crystal silicon light valve matrices provide high resolution images compatible with 35 mm optics.

In one preferred embodiment, an optically transmissive substrate is positioned to receive light from a back-light source and a light valve matrix is secured to the substrate. In accordance with the present invention, the light valve matrix includes an array of transistors and an array of electrodes. The light valve matrix also includes an adjacent light transmitting material, through which light from the back-light source is selectively transmitted. Preferred embodiments are directed to light valves employing a transmissive light transmitting material such as liquid crystal or a ferroelectric material, although other transmissive materials may be used. Each light valve includes a transistor, an electrode and a portion of the adjacent light transmitting material. Each transistor, by application of an electric field or signal, serves to control the optical transmission of light through the adjacent light transmitting material for a single light valve.

A driver circuit is electrically connected to the light valve matrix to selectively actuate the light valves. The drive circuitry may be formed in the same thin-film material in which the transistors and electrodes have been formed. The drive circuitry is capable of being fully interconnected to the light valve matrix using thin-film metallization techniques without the need for wires and wirebonding. An optical system is also provided for projecting light transmitted through the actuated light valves onto a large viewing surface.

The present devices and related methods for fabricating projectors satisfy the requirements of large screen television or monitor displays for producing highly defined color images. To that end, a projection display device can have multiple light valves each adapted to selectively transmit light of a single primary color. Further, a dichroic prism may be provided for combining the single color light transmitted by each light valve producing a multi-color light image which is projected onto a large viewing surface.

Other preferred embodiments of the present invention relate to an active matrix slide adapted for use in a conventional 35 mm slide projector for providing monochrome or multi-color images. The active matrix is mounted within a slide frame, which is fabricated to have equivalent physical dimensions as a standard 35 mm photographic slide having an image that can be projected by a slide projector. In accordance with the present invention, an active matrix slide assembly, being packaged to be size equivalent with a standard 35 mm slide, is insertable into a slide projector for generating the projected images. An electronics unit is connected to the active matrix and controls image generation by the active matrix. In preferred embodiments, the active matrix is capable of generating monochrome or multi-color images.

In one preferred embodiment of the invention, an active matrix display unit is adapted for use with a slide projector having a projector body, a light source, an optical system, and a projection chamber in which a 35 mm slide can be placed for projection of a fixed photographic image onto an external viewing surface. The display unit includes a housing and an active matrix slide assembly movably mounted to the housing. As such, the slide assembly has a storage position and an operating position. The housing is positioned on the slide projector body such that the slide assembly, being moved into the operating position, can be securely disposed in the projection chamber for selectively transmitting light from the light source to provide images for projection by the slide projector optics.

The housing preferably contains a shielded electronics assembly which is electrically connected to the active matrix for controlling image generation. The electronics assembly receives image data from an image generation device which can be a computer or any video source. Image data provided by the image generation device is processed by the electronics and sent to the active matrix. Responsive to the received data, the individual active matrix light valves are actuated such that illuminating light from the light source is selectively transmitted through the active matrix to form monochrome or multi-color images.

In another preferred embodiment, the active matrix display unit includes an active matrix slide assembly and a remote electronics housing. The active matrix slide assembly is dimensioned to be securely positioned in the projection chamber of the slide projector and is electrically connected to electronics in the remote housing by a cable.

In yet another preferred embodiment, the active matrix display unit includes an active matrix that is not physically connected to the electronics housing. Instead, the active matrix and the electronics in the housing communicate with each other via antenna elements such as RF antennas or infrared transmitter/detector elements.

As with aforementioned embodiments, an active matrix has an array of pixels or light valves that are individually actuated by a drive circuit. The drive circuit components can be positioned adjacent to the array and electrically connected to the light valves. As such, the individual light valves are actuated by the drive circuit so illuminating light is selectively transmitted through the slide to form an image.

BRIEF DESCRIPTION OF THE DRAWINGS

The above and other features of the invention, including various novel details of construction and combination of parts, will now be more particularly described with reference to the accompanying drawings and pointed out in the claims. It will be understood that the particular slide projector mountable light valve display embodying the invention is shown by way of illustration only and not as a limitation of the invention. The principles and features of this invention may be employed in varied and numerous embodiments without departing from the scope of the invention.

FIGS. 1A–D illustrate a preferred embodiment of the light valve housing with the light valve slide assembly retracted.

DETAILED DESCRIPTION OF A PREFERRED EMBODIMENT OF THE INVENTION

Figure 1C:
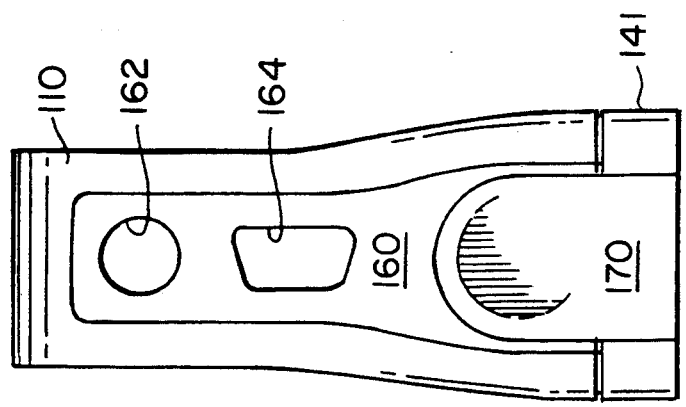

FIGS. 1A–D illustrate external feature of a slide projector mountable light valve display housing 100 according to a preferred embodiment of the invention. The housing 100 is adapted to be mounted to a commercially available slide projector. Commercially available slide projectors are available from Vivatar, Kodak, Agfa, and other manufacturers. A particular preferred embodiment of the invention will be described in relation to a Kodak carousel slide projector. It being understood that other slide projectors can be used with minor structural changes to the housing 100.

FIG. 1A is a right-side perspective view of a preferred embodiment of a slide projector mountable light valve slide housing 100. Illustrated is the housing body 110, a top control panel 112, a base 141, and a manual release access door 150. An infrared receiving element 114 is visible on the housing body 110. The control panel 112 contains a plurality of raised buttons 181 and a power indicator 183, such as an LED. The housing base 141 contains a frame tab channel 146 and a mounting lip 148. The housing 100 is ergonomically designed for an average human hand.

Figure 1B:
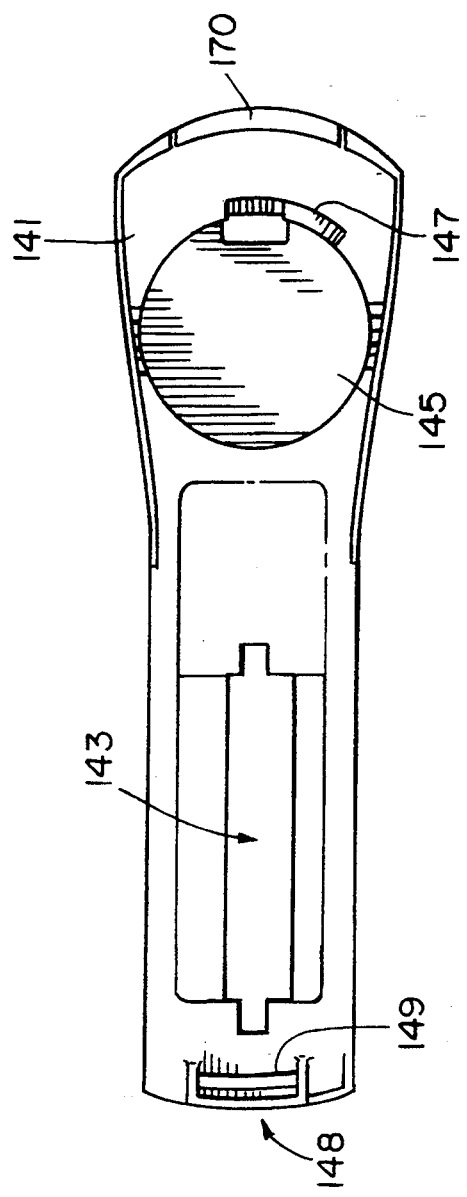

FIG. 1B illustrates a bottom plan view of the housing 100. A spindle mount 145 registers to the center hub of a slide projector. After the spindle mount 145 is mounted on the center hub, the housing 100 is rotated into position on the slide projector. A spindle tab cutout 147 and clip 146 are adjacent to the spindle mount 145 and registers to a spindle tab on the projector spindle. Once the housing 100 has been rotated into position, the mounting lip 148 registers to the slide projector housing. The mounting lip 148 also contains a mounting slot 149, which registers to a remote control unit (discussed below). Also shown is an opening to a slide channel 143 through which a light valve slide extends and retracts. The clip secures the housing to the center hub, once the housing 100 has been rotated into position. A remote control release 170 registers to the remote control unit. The clip 146 acts as a spring acting against the remote control release 170.

FIG. 1C is a rear view of the housing 100. Registered to the housing body 110 is an external interface plate 160 and the remote control release 170. The external interface plate 160 contains a power connector cutout 162 and a video signal connector cutout 164.

Figure 1D:
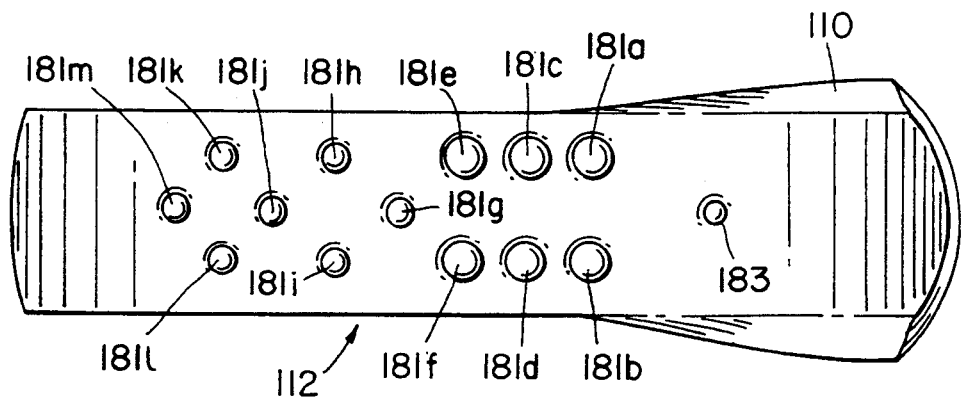

FIG. 1D is a top plan view of the housing 100. Shown are the elevated control buttons 181 and the power indicator 183. The control buttons allow the user to control brightness 181a, 181b, contrast 181c, 181d, and tuning 181e, 181f (i.e., pixel centering). A graphics/text button 181g allows the user to switch between graphics and text displays on an MS-DOS computer. Frame buttons 181j, . . . , 181m allow the user to shift the display up, left, right and down, respectively, by whole pixel increments. A save button 181h saves the current setting for the current video mode. A reset button 181i returns the settings to factory default settings. Each control panel button 181 is formed from a rubberized button insert (not shown), which is registered to a control panel contact pad insert (not shown).

Figure 2B:
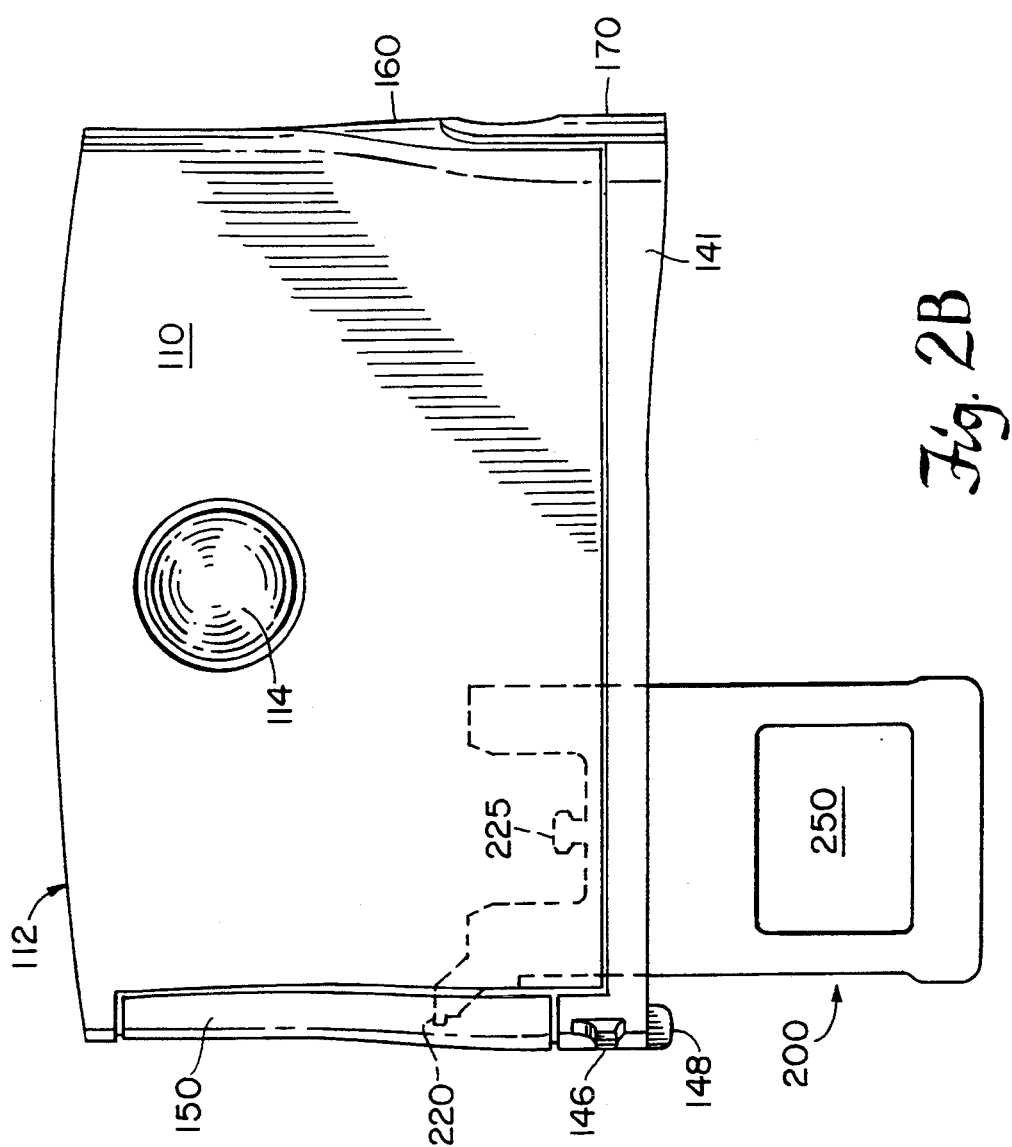
FIGS. 2A–B illustrate a preferred embodiment of the light valve housing with the light valve slide assembly extended.
Figure 2A:
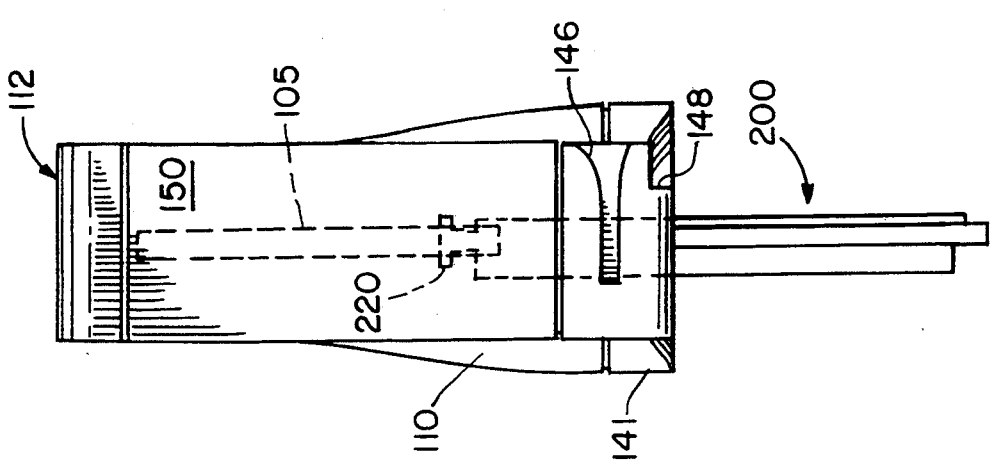

FIG. 2A is a front plan view of the housing 100 with a light valve slide assembly 200 in the extended position. Located behind the access door 150 is a handle slot 105 (shown in phantom). A slide handle 220 (shown in phantom) extends through the handle slot 105 and moves relative to the handle slot 105 as the light valve slide assembly 200 is moved within the housing 100.

FIG. 2B is a right-side plan view of the housing 100 with the light valve slide assembly 200 in the extended position.

Figure 3:
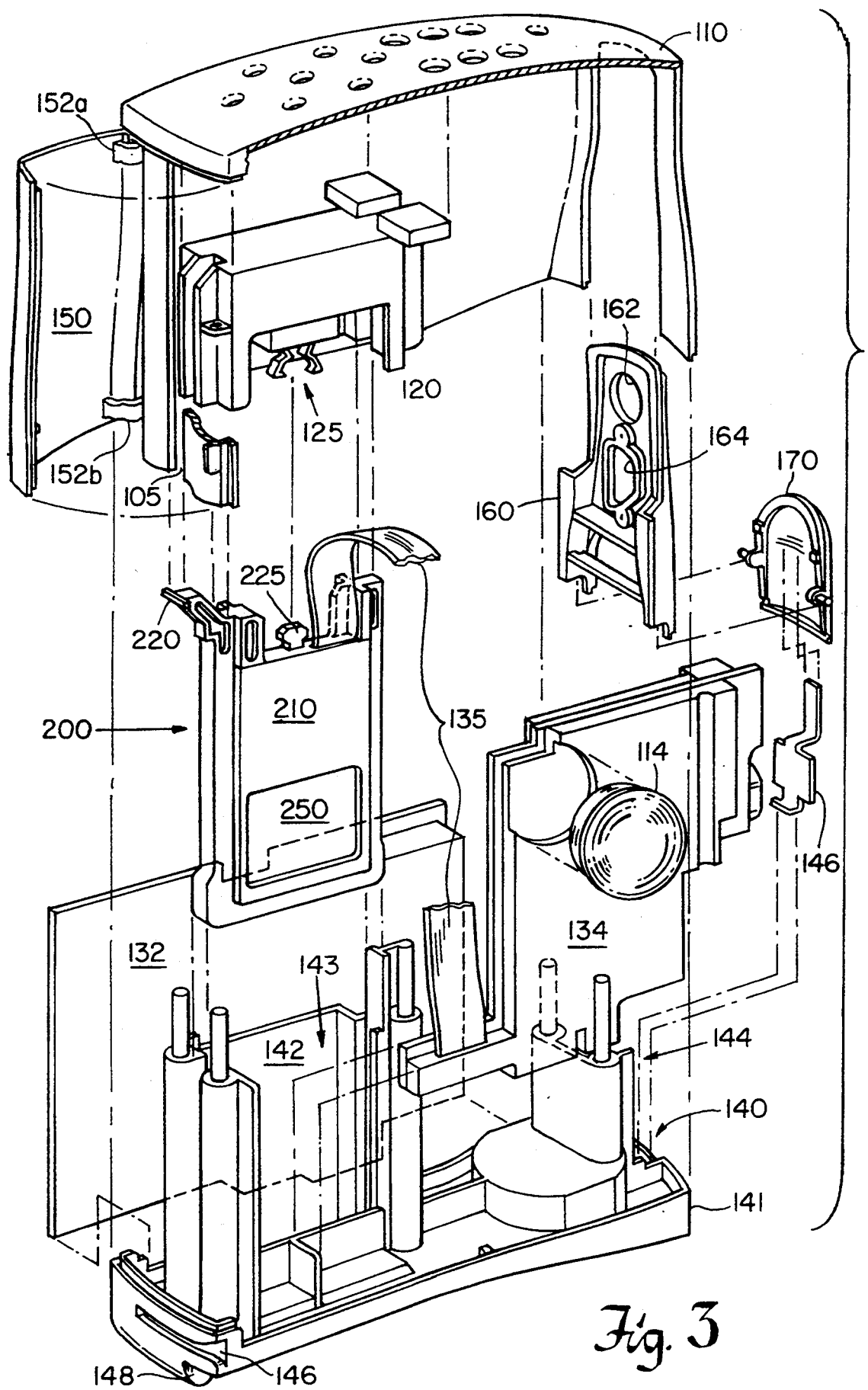
FIG. 3 is an exploded view of a preferred embodiment of a display unit.

FIG. 3 is an exploded view of a preferred display unit. A housing base 140 contains much of the structural elements of the housing 100. In particular, a front superstructure 142 a slide channel 143 for the light valve slide assembly 200 and provides structural support for the front of the housing 100. In addition, a rear superstructure 144 is mounted to the topside of the spindle mount 145 to provide structural support for the rear of the housing 100.

The light valve slide assembly 200 moves freely through the slide channel 143. A latch holder 120 registers to the slide channel 143. The latch holder 120 includes a latch mechanism 125. The latch mechanism 125 meets with a latch tab 225 of a light valve slide frame 210. When the light valve slide assembly 200 is fully retracted into the housing 100, the latch mechanism 125 secures the latch tab 225 so the light valve slide assembly 200 is fixed to the housing in the retracted position. The latch mechanism 125 is of a type that releases the latch tab 225 when an upward pressure is placed on the light valve slide assembly 200. After being released, the light valve slide assembly 200 descends through the slide channel 143. Preferably, the light valve slide assembly 200 is gravity fed.

During operation, it is possible that the light valve slide assembly 200 may jam while extended into the projection chamber 16. For that reason, the slide handle 220 can be accessed through the manual release access door 150, which is mounted to the housing body 110 by hinges 152a, 152b. By using the slide handle 220, a user can manually raise or lower the light valve slide assembly 200.

A light valve display panel 250 is coupled to video control circuitry 132, 134. As illustrated in FIG. 3, the video control circuitry is provided by a digital circuit board 132 and analog circuit board 134. In particular, the analog circuit board 134 is a daughter board connected to the digital circuit board 132. These circuit boards 132, 134 are adapted to fit within the housing 100. The analog circuit board 134 receives power from an external power source and analog video signals from an external video source through power cutout 162 and video connector cutout 164, respectively. Preferably, the video source is a computer that generates video images. The video source can generate a composite video signal. The analog circuit board 134 also receives user control signals from the control panel 12 and the remote control unit 300. The digital circuit board 132 performs digital processing of the video signal. The drive signals for the light valves are provided by the analog circuit board 134 over a ribbon cable 135.

Figure 4A:
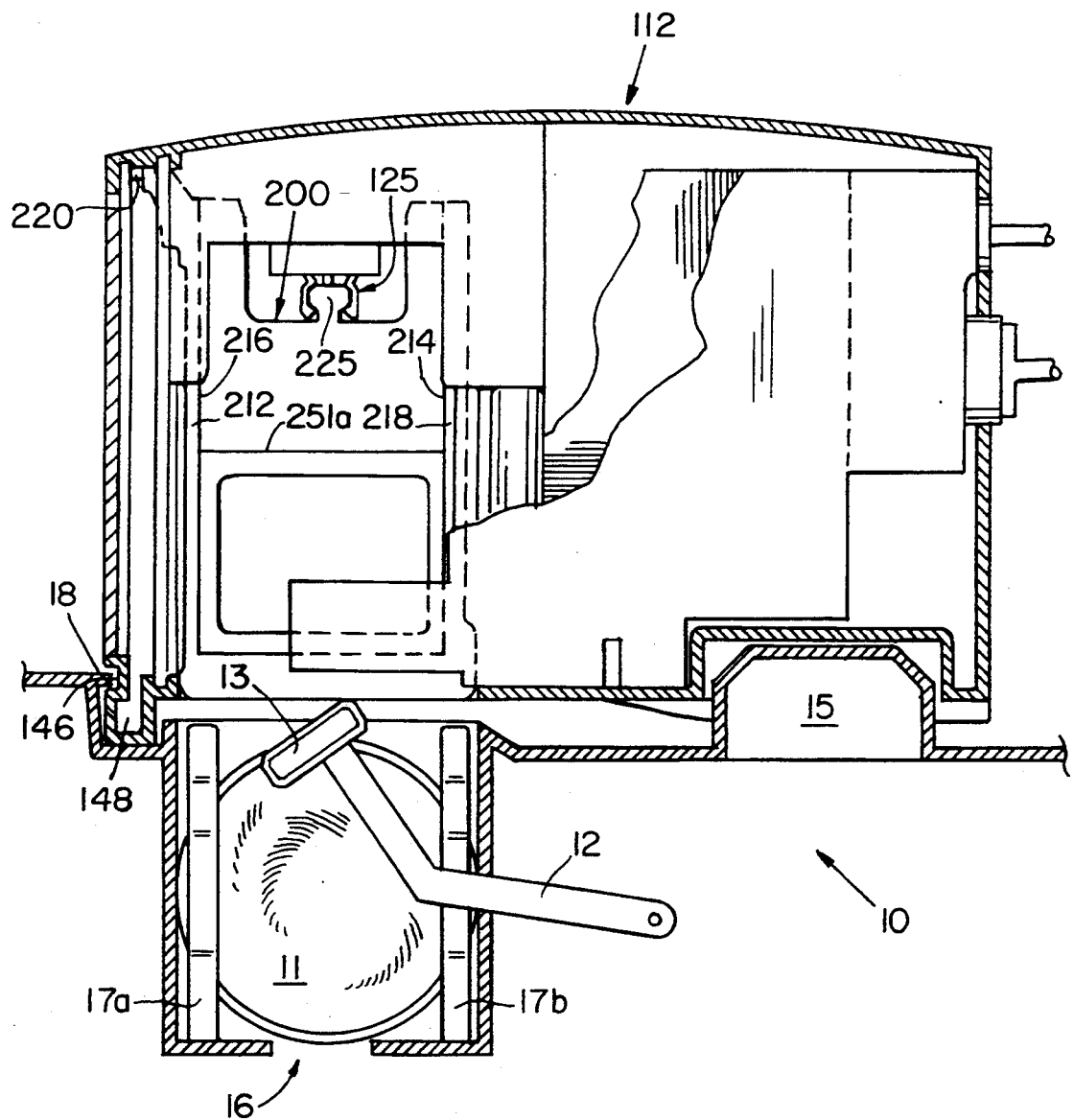
FIGS. 4A–B are sectional views of a preferred light valve display unit mounted on a standard slide projector.

FIG. 4A illustrates the housing 100 properly aligned in the locked position with the light valve slide assembly 200 aligned directly above the projection chamber 16 of the projector 10. Once positioned and locked, the light valve slide assembly 200 is ready to be lowered into the projection chamber 16. By advancing the slide projector, the ejector arm 12 is raised such that the slide bumper 15 contacts the light valve slide 200. The upward motion of the ejector arm 12 urges the light valve slide assembly 200 vertically upward causing the latch mechanism 125 to disengage the latch tab 225. After being released from the latch mechanism 125, the light valve slide assembly 200 is supported by the slide bumper 13. The ejector arm 12 then continues to cycle downward to lower the light valve slide assembly 200 into the projection chamber 16. The light valve slide assembly 200 is secured by spring clips 17 in the projection chamber 16. Because of friction between the light valve slide assembly 200 and the slide channel 143, the light valve slide assembly may drop into the projection chamber 16 after the ejector arm 12 has finished the ejection cycle. On the next ejection cycle, the light valve slide assembly 200 will be forced upward by the ejector arm 12 to be secured by the latch mechanism 125.

Figure 4B:
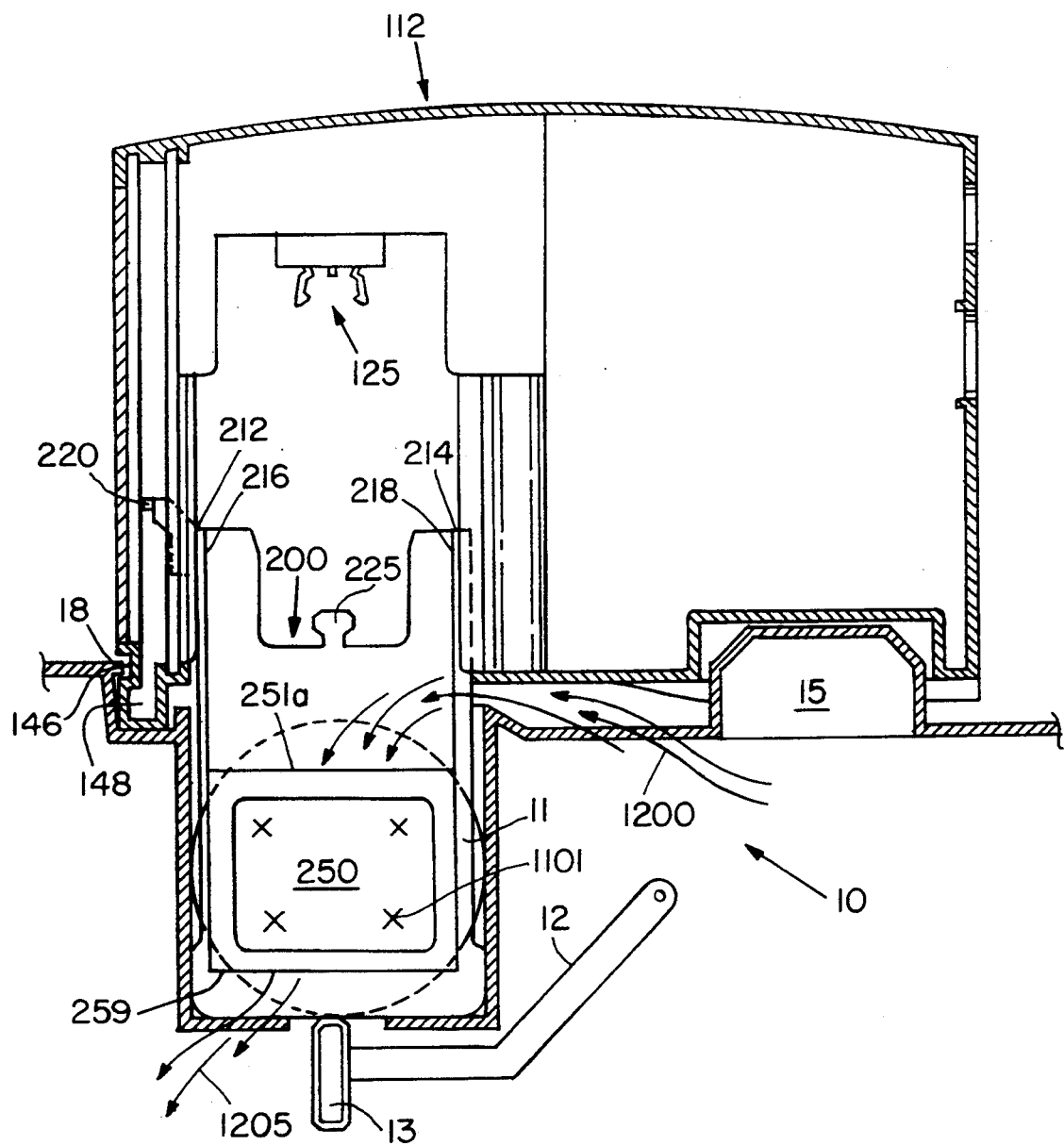

FIG. 4B illustrates the light valve slide assembly 200 positioned and retained in the projection chamber 16 of a slide projector 10, such that light 1101 from a light source (not shown) passes through the light valve 250 and is projected onto a viewing surface by a projection lens 11. While the light valve slide assembly 200 is positioned in the projection chamber 16, the light valve and associated circuitry are exposed to heat from the projector light source. Adequate ventilation must be provided to reduce the exposure of the light valve to excessive heat.

Ventilation is preferably provided through the underside of the housing 100. Cool air 1200 is drawn into the projection chamber 16 by a circulating fan (not shown) of the slide projector. The cool air 1200 is drawn through a ventilation channel 259 of the light valve slide assembly 200. Warm exhaust air 1205 exits the ventilation channel 259 and is expelled by the projector circulating fan. The physical characteristics of the ventilation channel 259 will be discussed in more detail below.

Figure 5A:
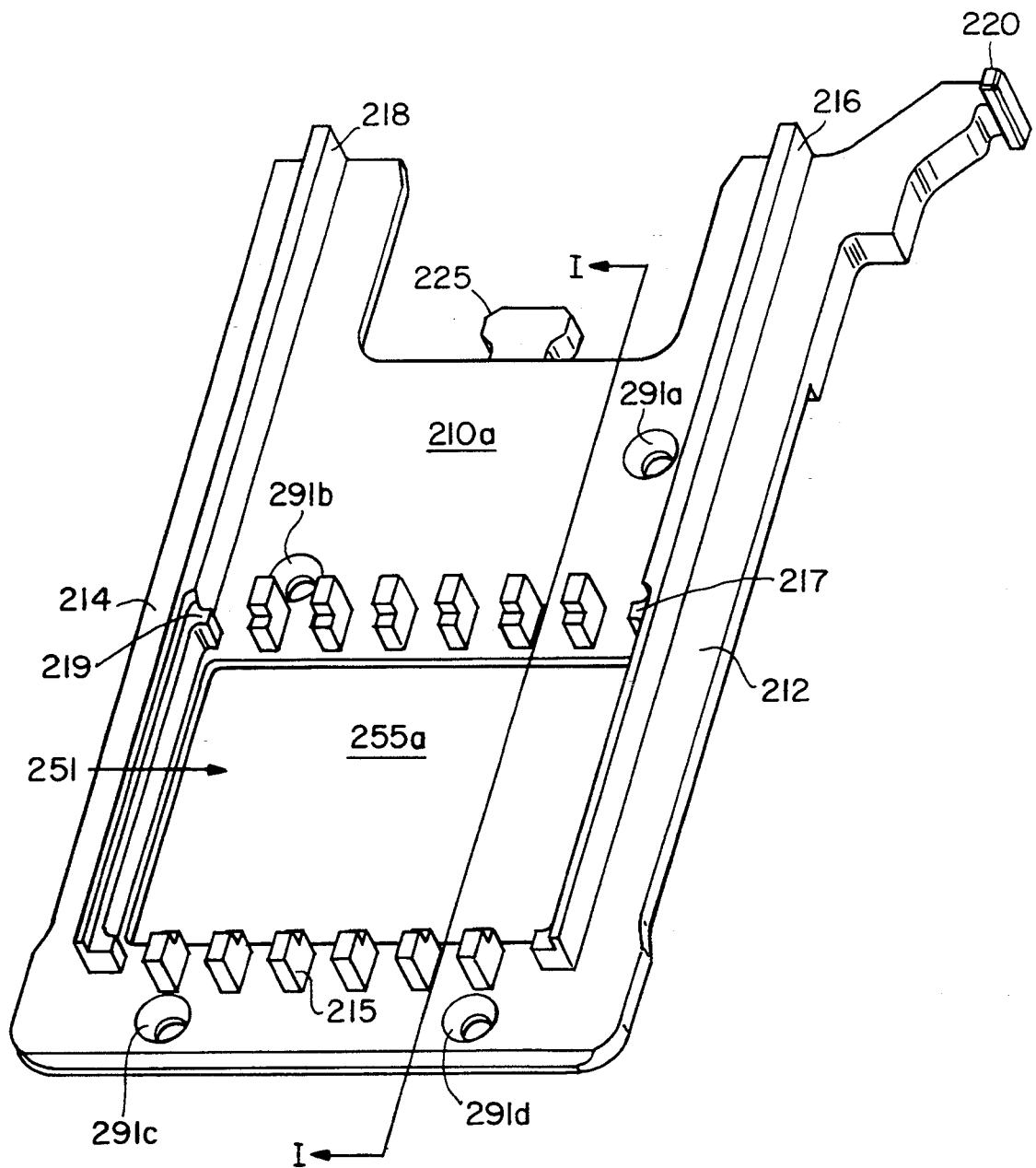
FIGS. 5A–C are perspective views of the light valve slide frame 210 of FIG. 3.
Figure 5B:
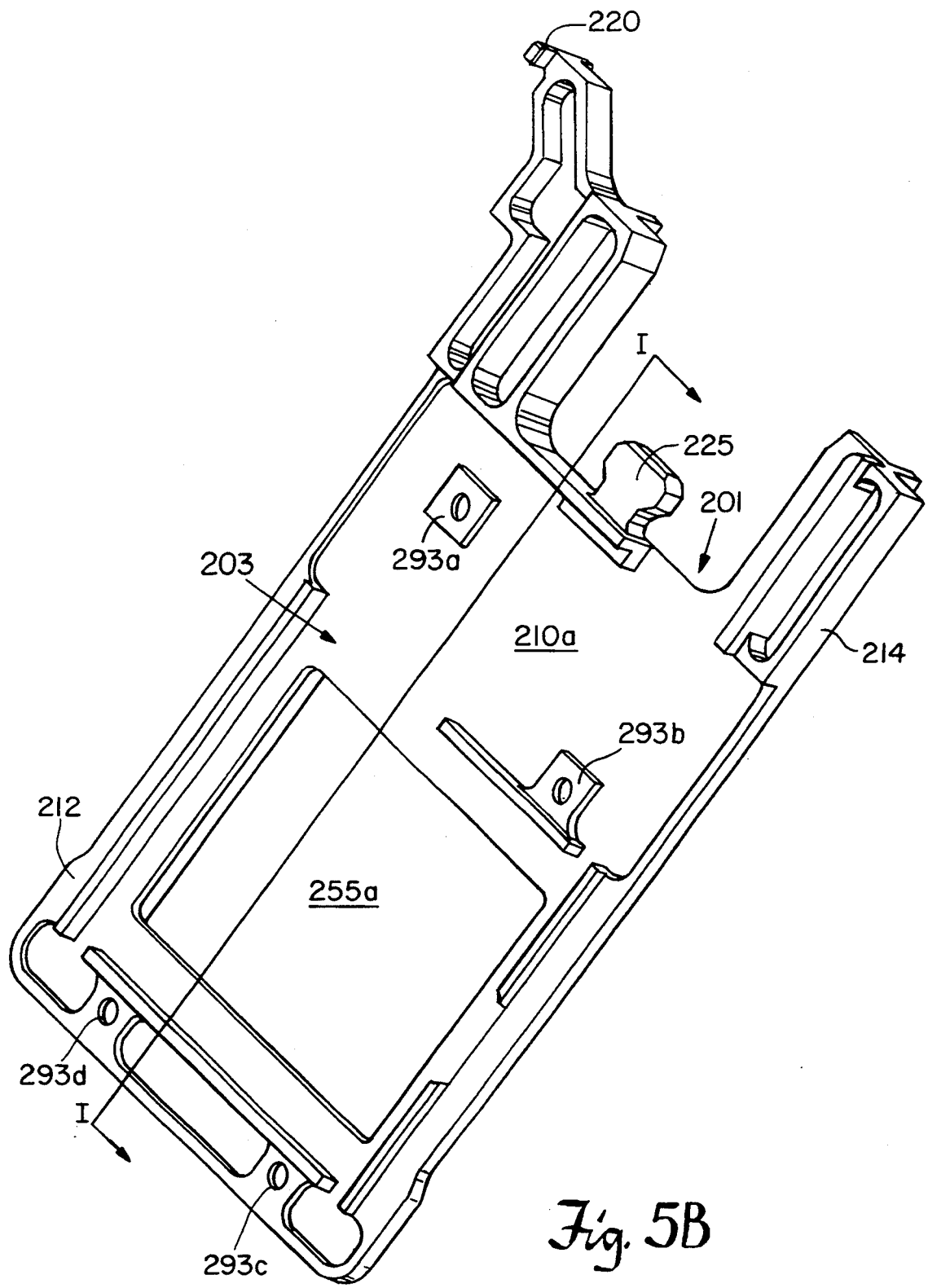
Figure 5C:
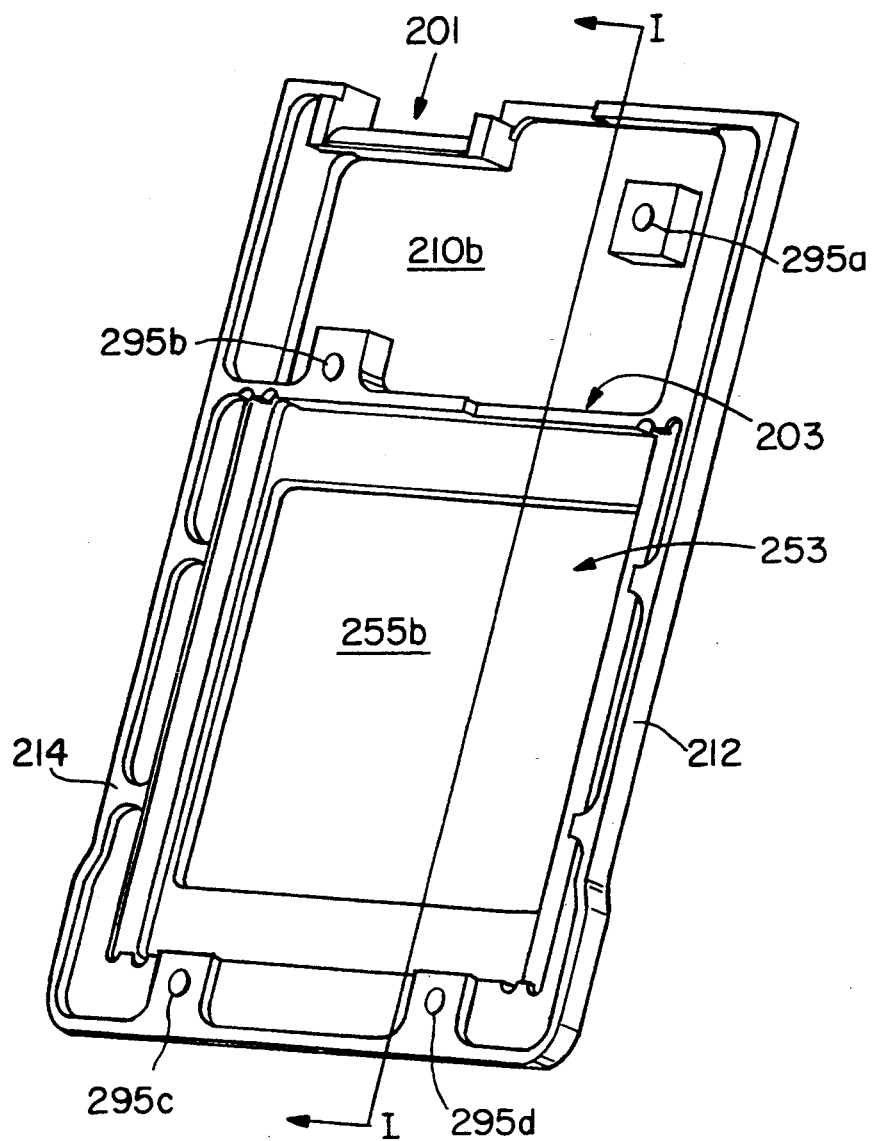

Critical features of the construction of the light valve slide assembly 200 are illustrated in FIGS. 5A–5C, which are perspective views of the light valve slide frame 210 of FIG. 3. The slide frame 210 comprises two main structural features. The main structural element is the display holder 210a shown in FIGS. 5A–5B. The second main structural element is the display cover 210b, which is illustrated in FIG. 5C. As will be described in detail below, the display holder 210a and the display cover 210b are sandwiched together with a light valve display panel 250 disposed between the two elements.

FIG. 5A is a perspective view of the light-source side of the display holder 210a. Illustrated are a front rail 212 and a rear rail 214. The rails 212, 214 register to corresponding rail slots in the slide channel 143. The rails 212, 214 and the rail slots cooperate to allow and facilitate movement of the light valve slide assembly 200 into and out of the housing 100 while inhibiting twisting or lateral motion of the light valve slide assembly 200. The handle 220 is fastened to the front rail 212. Also illustrated are a front stop 216 and a rear stop 218. These stops work in conjunction with the rails 212, 214. A polarizer area 251 is defined between the stops 216, 218. The polarizer area 251 is registered to the display aperture 255a. The polarizer area 251 is spatially displaced from the viewing aperture 255a such that a ventilation channel is formed between the polarizer area 251 and the viewing aperture 255a. A polarizer 252 is supported by ledges 217, 218 of the stops 216, 218. Further support for the polarizer 252 can be provided by spacer support 215. There may be fewer or more spacer supports 215 than illustrated in FIG. 5A. Finally, a plurality of recessed fastening apertures 291 are shown for receiving a fastener, such as a bolt.

FIG. 5B is a perspective view of the backside of the display holder 210a of FIG. 5A. In particular, note the signal cable feed through ports 201, 203. The signal cable from the analog circuit board 134 is fed through the upper feed through port 201 and through the lower feed through port 203 to connect to a light valve display. Note that each fastening hole has a fastening support 293.

FIG. 5C is a perspective view of a display cover 210b. Again, note the upper feed through port 201 and the lower feed through port 203. The display cover 210b has formed therein a display panel area 253. The liquid crystal display panel 250 registers to the display panel area 253 such that when the display cover is fastened to the display holder 210a, the light valve display panel is fixedly aligned with the view aperture 255. Fastening nuts 295 are intrically formed in the display cover 210b.

In a preferred embodiment of the invention, both the display holder 210a and the display cover 210b are fabricated from zinc. Zinc is chosen because of suitability to casting. Other materials may be substituted instead of zinc. However, the materials of the light valve slide frame 210 should be compatible with the materials used to form the slide channel 143 of the display housing 100. In particular, the coefficient of friction between the two materials should be low enough so that the light valve slide 200 can freely descend and ascend through the slide channel 143. In a preferred embodiment of the invention, the slide channel 143, as well as the housing 100, is fabricated from injection molded plastic.

Figure 5D:
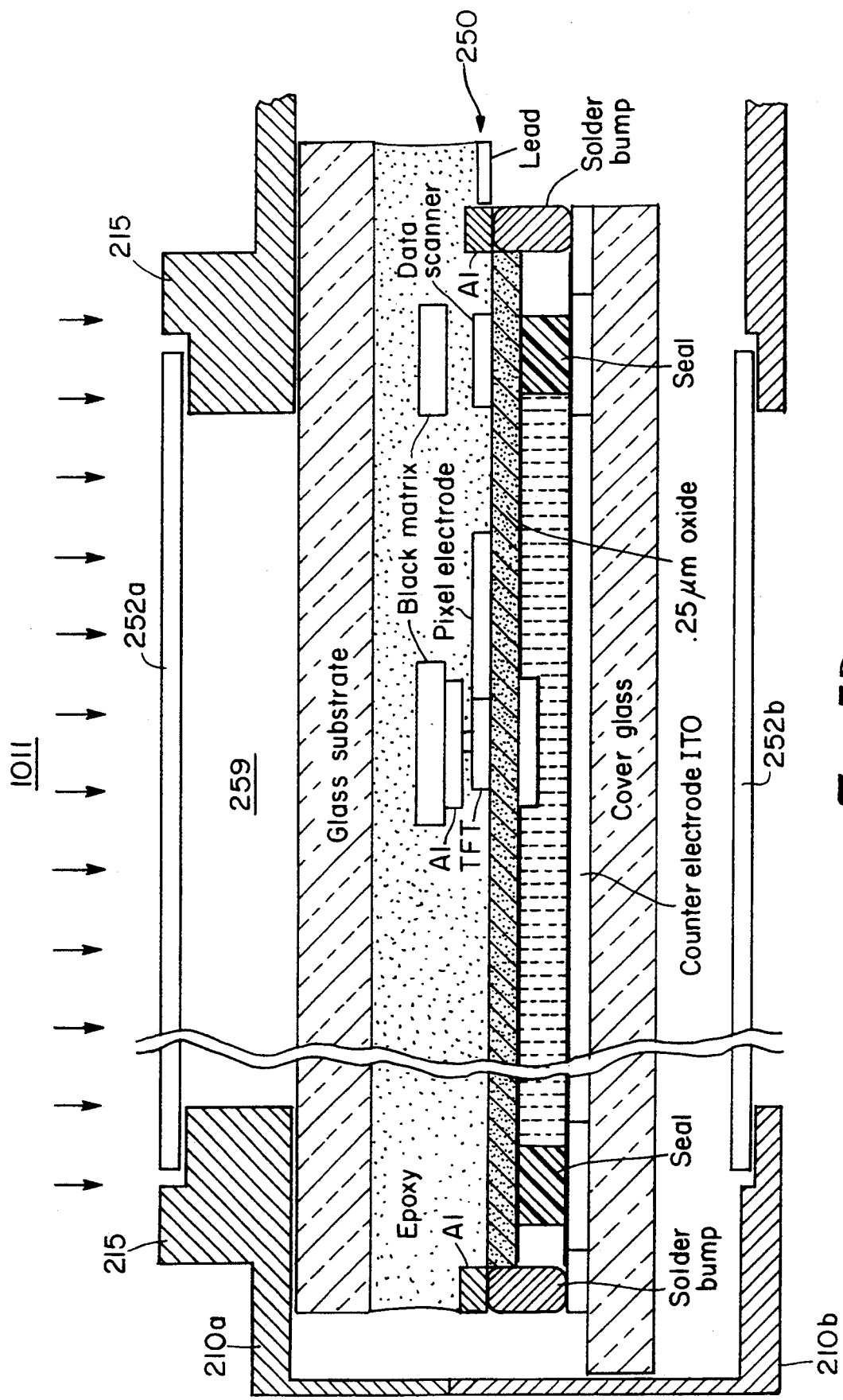
FIG. 5D is a partial schematic cross sectional view of a mounted display panel 250 taken along lines I—I of FIGS. 5A–C.

FIG. 5D is a cross-sectional view of a mounted display panel 250 taken along section lines I—I of FIGS. 5A–5C. The display panel 250 is sandwiched between the display holder 210a and the display cover 210b. In a preferred embodiment, the display panel 250 is an active matrix liquid crystal display. It is understood that the display panel 250 could be a passive matrix liquid crystal display, or another suitable light transmissive light valve display. Note the ventilation channel 259 formed between the polarizer 252 and the active matrix 250.

Figure 6A:
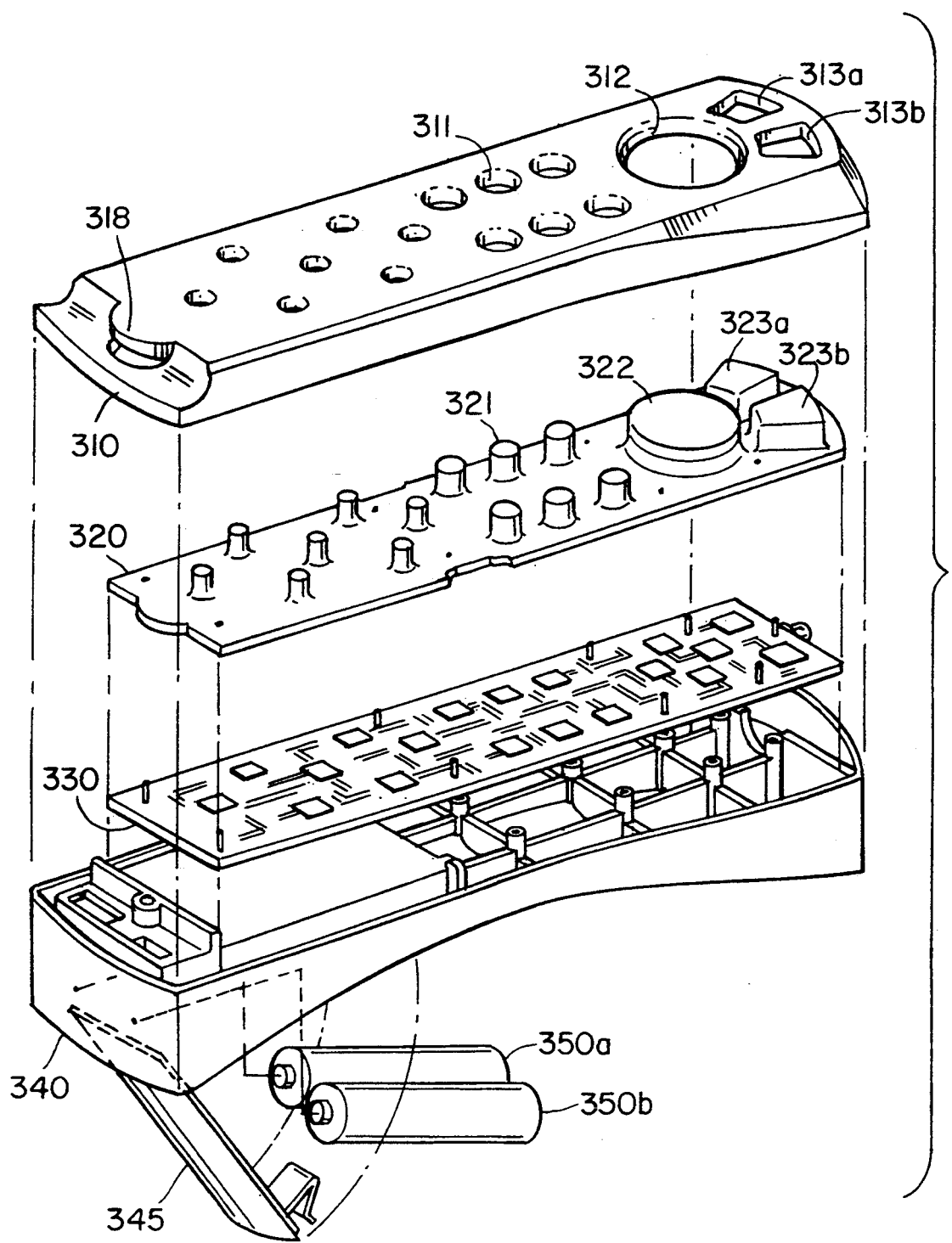
FIG. 6A is an exploded view of remote control units.

FIG. 6A is an exploded perspective view of a remote control device 300 for use in controlling the displayed image.

Typically, the remote control unit 300 is defined by an upper shell 310 and a lower shell 340. The upper shell 310 contains a plurality of voids 312, 314, 316 through which control buttons 322, cursor control button 324, and mouse select buttons 326 are accessed, respectively. The buttons 322, 324, 326 are preferably rubberized buttons molded onto a rubberized button insert 320. The buttons 322, 324, 326 are registered to contact pads 332, 334, 336 on a circuit board 330. In response to user inputs through the control buttons 322, 324, 326, an infrared signal is generated by LED 339. The infrared signal transmits the user's selections to housing 100.

The remote 300 is preferably powered by batteries 350 installed within a battery chamber in the lower segment 340 and secured therein by a battery door 345. The batteries preferably provide three-volts to the circuit board 330. It being understood that alternate battery configuration can be utilized instead, such as a nine-volt battery.

Figure 6B:
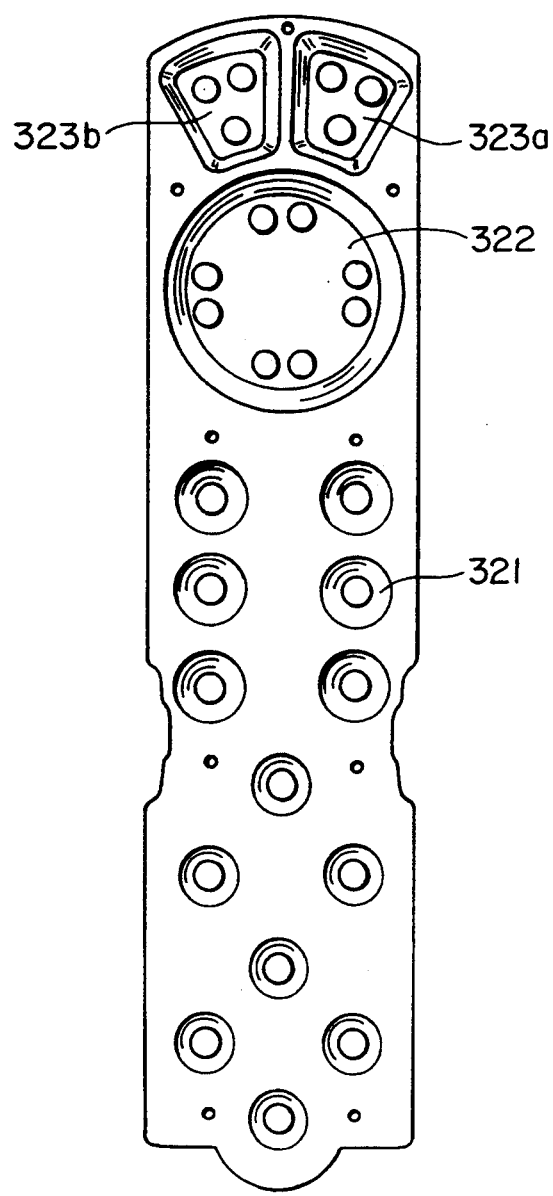
FIG. 6B is a view of the underside of the button insert 320 of FIG. 5A.

FIG. 6B is a view of the underside of the rubberized button insert 320. Each button 322, 324, 326 has at least one button contact protrusion for depressing an associated contact pad 332, 334, 336. Each control button 322 has a single button contact protrusion 333. Each mouse select button 326 has three redundant button contact protrusions 327. The mouse select buttons 326 preferably emulates standard Microsoft or Apple mouse select buttons. The functions of the select buttons 326 can be programmed to differ from standard mouse select buttons. For example, the right select button 326b can function as a drag-lock. The cursor control button 324 provides for eight-way cursor movement. There are, however, only four cursor control contact pads 334 to provide the eight-way cursor movement.

In a preferred embodiment, the cursor control button 324 has eight button contact protrusions 325. The cursor control contact protrusions 325 are paired with respective contact pads 334 such that a user selection of left, right, up or down results in a redundant depression of the respective contact pad 334. Each pair of cursor control contact protrusions are further positioned such that a diagonal user selection results in the depression of the two contact pads 334 adjacent to the diagonal direction. A processing unit interprets the depression of adjacent contact pads 334 as a diagonal cursor movement.

In another preferred embodiment, the cursor control button 324 is a plastic cap (such as a rigid disk or ring), which is registered to four directional buttons. Each directional button is registered to a respective cursor control contact pad 334. As pressure is placed on an area of the plastic cap, at least one directional button is depressed to contact a cursor control contact pad 334. If the depressed area of the plastic cap is about midway between two adjacent directional buttons, then both adjacent directional buttons are depressed. Processing similar to that discussed above, interprets this as a diagonal cursor movement.

In other preferred embodiments, cursor control is provided through a trackball or joystick dimensioned for use with the remote control 300 of course discrete cursor control keys can also be used with the remote control 300.

The remote control buttons 322 perform the same functions as the control panel buttons 181.

Figure 7:
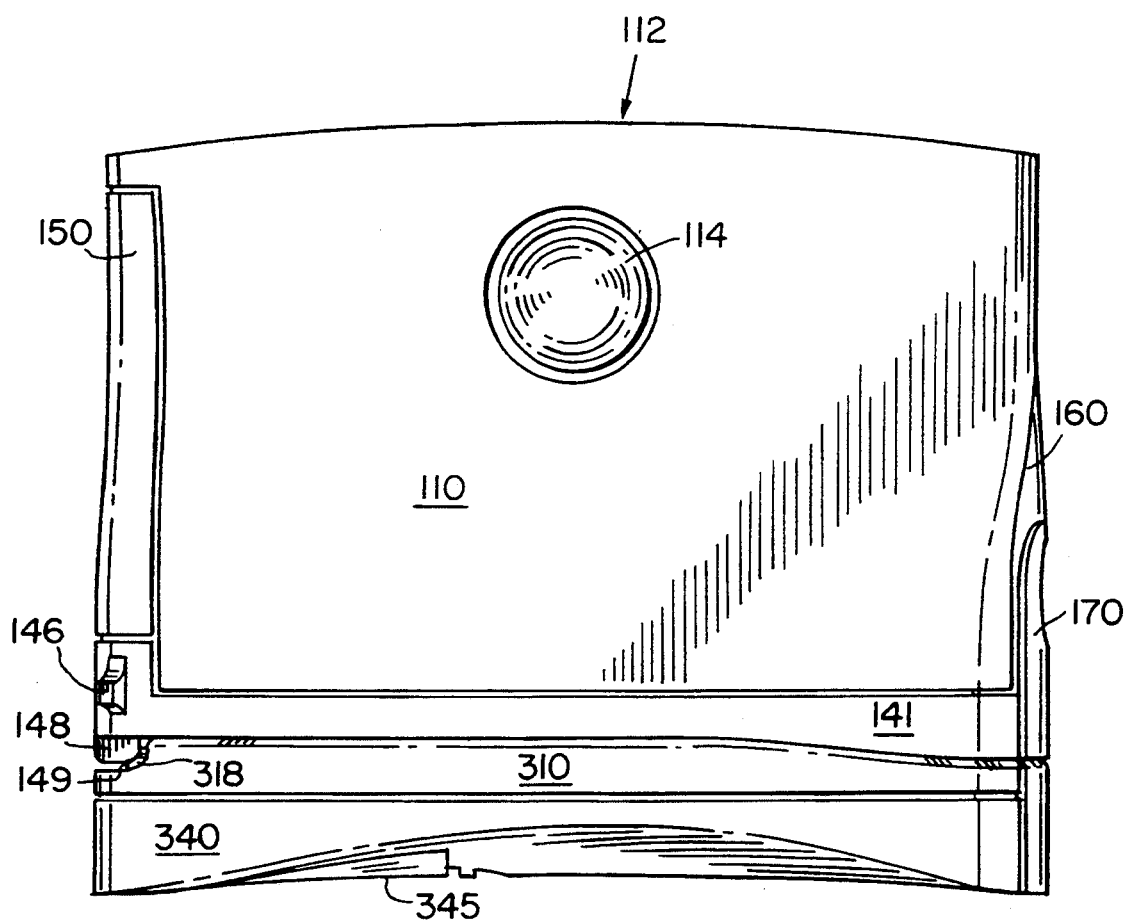
FIG. 7 illustrates a preferred embodiment of the housing with an attached remote control unit.

FIG. 7 is a right side view of the housing 100 with an attached remote control unit 300. The remote control device 300 registers to the base 141 of the housing 100, such that the remote control device 300 attaches to and stores underneath the housing 100 when the light valve slide 200 is in the upward position. In particular, a mounting tab 318 registers to the mounting slot 149 of the housing 100. The remote control device 300 is disengaged from the housing 100 by depressing the remote control release 170 on the housing 100.

Equivalents

While this invention has been particularly shown and described with reference to preferred embodiments thereof, it will be understood by those skilled in the art that various changes in form and details may be made therein without departing from the spirit and scope of the invention are defined by the appended claims.

We claim:

1. A housing for a slide projector mounted light valve display comprising:
   a housing having a securing mechanism to secure the housing to the slide projector; and
   a light valve slide assembly movable between a first position within the housing and a second position outside the housing in response to a slide ejection cycle of the slide projector.

2. The housing of claim 1 wherein the securing mechanism registers to a spindle of the slide projector.

3. The housing of claim 1 wherein the securing mechanism registers to a frame tab of the slide projector.

4. The housing of claim 1 wherein the light valve slide assembly includes an active matrix liquid crystal display.

5. The housing of claim 1 further comprising a movement switching mechanism registered to the light valve slide assembly and actuated by movement of an ejector arm of the slide projector.

6. The housing of claim 5 wherein the movement switching mechanism is actuable by a manual control.

7. The housing of claim 1 further comprising a video interface coupled between the active matrix slide assembly and a remote video source.

8. The housing of claim 7 wherein the video source is a computer, which generates video images.

9. The housing of claim 7 wherein the video source generates a composite video signal.

10. The housing of claim 7 further comprising a remote control receiver, the video source being responsive to remote control signals received by the receiver.

11. The housing of claim 10 wherein the remote control receiver comprises an infrared detector.

12. A housing for a slide projector mounted light valve display comprising:
    a housing adapted to be positioned on a slide projector assembly;
    a light valve slide assembly movable through an aperture in the housing between a first position within the housing and a second position outside the housing; and
    a switching mechanism for controlling movement of the light valve slide assembly between the first position and the second position in response to a slide ejection cycle of the slide projector.

13. The housing of claim 12 wherein the light valve slide assembly includes an active matrix liquid crystal display.

14. The housing of claim 12 wherein the switching mechanism is automatically actuated in response to operation of the slide projector.

15. A method of operating a slide projector mounted light valve display comprising the steps of:
    securing a light valve housing to a slide projector; and
    moving a light valve slide assembly between a first position within the housing and a second position outside the housing in response to a slide ejection cycle of the slide projector.

16. The method of claim 15 wherein the securing step comprises registering the housing on a spindle of the slide projector.

17. The method of claim 15 wherein the moving step comprises operating the slide projector to move the light valve slide assembly from the first position to a position in a projection chamber of the slide projector.

18. The method of claim 15 the moving step comprises operating the slide projector to move the light valve slide assembly from a position in a projection chamber of the slide projector to the first position.

19. A method of operating a slide projector mounted light valve display comprising the steps of:
    securing a light valve housing to a slide projector;
    securing a light valve slide assembly to a latch mechanism when in a first position within the housing; and
    moving the light valve slide assembly between the first position and a second position outside the housing in response to a slide ejection cycle of the slide projector.

20. The method of claim 19 further comprising the step of alternately releasing and securing the light valve slide assembly to the latch mechanism in automatic response to successive slide ejection cycles.

* * * * *